(12) United States Patent
Repo et al.

(10) Patent No.: US 6,362,356 B1
(45) Date of Patent: Mar. 26, 2002

(54) METALLOCENE COMPOUNDS FOR THE POLYMERIZATION OF ETHYLENICALLY UNSATURATED MONOMERS

(75) Inventors: Timo Repo, Helsinki; Markku Leskelä, Espoo, both of (FI)

(73) Assignee: Borealis A/S, Lyngby (DK)

( * ) Notice: Subject to any disclaimer, the term of this patent is extended or adjusted under 35 U.S.C. 154(b) by 0 days.

(21) Appl. No.: 09/462,640

(22) PCT Filed: Jul. 9, 1998

(86) PCT No.: PCT/FI98/00581

§ 371 Date: Jan. 11, 2000

§ 102(e) Date: Jan. 11, 2000

(87) PCT Pub. No.: WO99/02540

PCT Pub. Date: Jan. 21, 1999

(30) Foreign Application Priority Data

Jul. 11, 1997 (FI) .................................. 972946

(51) Int. Cl.[7] .............................. C07F 17/00; C07F 7/00; B01J 31/00; C08F 4/44
(52) U.S. Cl. .......................... 556/53; 556/11; 556/12; 556/43; 526/160; 526/943; 502/103; 502/117
(58) Field of Search .................. 556/43, 53, 11, 556/12; 502/103, 117; 526/160, 943

(56) References Cited

FOREIGN PATENT DOCUMENTS

| EP | A10549900 | 7/1993 |
| EP | A10672675 | 9/1995 |
| EP | A20754698 | 1/1997 |
| FI | A950709 | 9/1995 |

OTHER PUBLICATIONS

Goedheijt et al., Organometallics, vol. 13, No. 8, pp. 2931–2933 (1994).*

Bernhard Rieger, Polymer Bulletin, vol. 35, 1995, pp. 87–94.

* cited by examiner

Primary Examiner—Porfirio Nazario-Gonzalez
(74) Attorney, Agent, or Firm—Birch, Stewart, Kolasch & Birch, LLP

(57) ABSTRACT

The invention relates to metallocen compounds having $\eta^5$ ligands comprising at least four fused rings and having a sum of fused rings in all of its $\eta^5$ ligands being at least 6. Such compounds are for example {[1-(7,9-diphenylcyclopent[a]acenaphthadienyle)-1-phenyle-2-(7,9-diphenylcyclopent[a]acenaphthadienyl)]ethane} zirconium dichloride, {[1-(7,9-diphenycyclopent[a]acenaphthadienyl)-1-phenyl-2-flourenyl]ethane} zirconium dichloride, [bis(7,9-diphenylcyclopent[a]acenaphthadienyl)] zirconium dichloride and [bis(7,9-diphenylcyclopent[a]acenaphthadienyl)]hafnium dichloride. The invention also relates to a catalyst composition comprising such as an aluminoxane. The metallocene compound and the catalyst composition can successfully be used to produce high molecular weight polyethene and long-chain branch polypropene.

55 Claims, No Drawings

METALLOCENE COMPOUNDS FOR THE POLYMERIZATION OF ETHYLENICALLY UNSATURATED MONOMERS

This application is the national phase under 35 U.S.C. §371 of PCT International Application No. PCT/FI98/00581 which has an International filing date of Jul. 9, 1998 which designated the United States of America.

The present invention relates to novel metallocene compounds based on a transition metal (Groups 3–10 of the Periodic Table (IUPAC 1990)). The invention also relates to polymerization catalyst compositions comprising a metallocene compound selected from said metallocene compounds and an aluminoxane. Further, the invention relates to a process for polymerizing at least one ethylenically unsaturated monomer such as an olefin in the presence of a metallocene compound, selected from said metallocene compounds, and an aluminoxane.

Metallocene stands for metal complexes having at least one isocyclic or heterocyclic η-cyclopentadiene ligand or at least one ligand structurally including isocyclic or heterocyclic η-cyclopentadiene. Such an η-cyclopentadiene ligand or ligand structurally including η-cyclopentadiene is below called an $\eta^5$ ligand, because all 5 cyclopentadienyl ring carbons are, without limiting the scope of protection, assumed to be essentially equally bound to the transition metal. Transition metals are elements with an incomplete d-shell in their atoms. They are metals of Groups 3–10 of the Periodic Table (IUPAC 1990). Aluminoxane stands for compounds having units of organometallic aluminium bound to oxygen.

Chiral bis(indenyl) ansa-metallocenes are well known catalyst components for polymerizations of alpha olefins. The performance of these metallocenes are different, depending on the metal used and the size and structure of the ligands, above all its $\eta^5$ ligands. For the production of isotactic polypropene, $C_2$-symmetric ethylene-bridged bis-indenyl zirconocene dichloride can be regarded as a key structure. It was first reported by Brinzinger et al. in 1982 (Wild, F. R. W. P., Zsolnai, I., Huttner, G., Brintzinger, H. H., J. Organomet. Chem. (1982) 232:233). Syndiotactic polypropene was prepared in 1988 using $C_S$-symmetric methylene-bridged fluorenyl cyclopentadienyl zirconocene dichloride. See Ewen, J. A., Jones, R. L., Razavi, A., Ferrara, J. D., J. Am. Chem. Soc. (1988) 110:6255.

Metallocenes having bulkier $\eta^5$ ligands have also been prepared and investigated. Unsymmetric ethylene-bridged 7,9-diphenylcyclopent[a]acenaphthadienyl cyclopentadienyl zirconocene dichloride was used together with methylaluminoxane (MAO) for propene polymerization. It produces atactic polypropene with high activity. See Rieger, B., Repo, T., Jany, G., Polymer Bulletin 35 (1995) 78–94.

The above mentioned metallocenes are primarily suitable for the polymerization of polypropene. The successful production of polyethene, and in particular high molecular weight polyethene (molecular weight of the magnitude up to one million), using metallocenes of the above type, has not been reported. Thus, the purpose of the invention is to find a suitable metallocene for the production of high molecular polyethylene in good yields.

The above mentioned prior metallocenes are primarily suitable for the polymerization of linear or short chain branched polypropene. The successful production of long chain branched polypropene, using metallocenes of the above type, has not been reported. Thus, an additional purpose of the invention is to find a metallocene for the production of long chain branched polypropene in good yields.

The above purposes of the invention has now been achieved with a metallocene compound based on a transition metal (of Groups 3–10 of the Periodic Table (IUPAC 1990)), which metallocene compound is essentially characterized in that at least one of its $\eta^5$ ligands comprises at least four fused rings including the $\eta^5$ bound cyclopentadiene ring and that the sum of fused rings in all of its $\eta^5$ ligands is at least 6.

Thus, it has been realized that a metallocene compound having more than a certain number fused rings in one and all of its $\eta^5$ ligands give high molecular weight polyethene in good yields. It has also been found that such a metallocene gives vinyl terminated polypropene, which via its reactive vinyl group forms, or is able to form, a polypropene having long chain branches. These two technically relevant functional properties distinguish the metallocene compounds of the invention from e.g. the metallocene compounds of above mentioned Rieger, B., Repo, T., lany, G., Polymer Bulletin 35 (1995) 78–94.

In its widest scope, the present document claims metallocenes of transition metals (metals of Group 3–10 of the Periodic Table) having a certain minimum number of fused rings including the cyclopentadiene ring in one and all of its $\eta^5$ ligands. However, according to a preferred embodiment of the invention, the metallocenes are based on transition metals of Groups 4–6, preferably Groups 4 and 5 of the Periodic Table (IUPAC 1990). Especially preferred transition metals are the Group 4 metals titanium, zirconium and hafnium, even more preferred zirconium and hafnium. Generally, the most preferred transition metal is zirconium.

According to the invention, the number of fused rings in at least one of the metallocene's $\eta^5$ ligands is at least four. The fused rings may be 5- and 6-membered rings, which are isocyclic or heterocyclic, for example containing up to 4 ring heteroatoms selected from O, N, S and P. By the terms "isocyclic" and "heterocyclic" is meant cyclic having only carbon ring members and cyclic having ring members of carbon and at least another element, respectively. The fused rings are preferably aromatic, but they can also be hydroaromatic, i.e. partially or completely hydrogenated (alicyclic). Typically, such $\eta^5$ ligands are four ring $\eta^5$ ligands, e.g. cyclopent[a]-as-indacenadienyl, cyclopent[a]-s-indacenadienyl, cyclopent[a]acenaphthadienyl, and five ring $\eta^5$ ligands, e.g. cyclopent[d]-acephenathradienyl, cyclopent[a]aceanthradienyl.

According to a preferred embodiment of the invention, the $\eta^5$ ligand of the metallocene comprising at least four fused rings is a ligand having the formula (I)

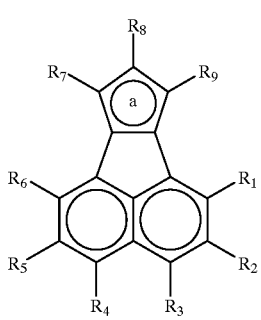

(I)

wherein each same or different of groups $R_1$–$R_9$ is one of hydrogen, a halogen and an organic group having from 1 to 20 carbon atoms, or at least one pair of adjacent groups from $R_1$–$R_9$ form together an organic ring structure having from 5 to 20 carbon atoms, one of $R_7$–$R_9$ being optionally replaced by a bridge to another $\eta^5$ ligand, and a indicates the $\eta^5$ bound cyclopentadienyl ring of said $\eta^5$ ligand comprising at least four fused rings; or is a hydroaromatic derivative ligand thereof.

Organic group or organic ring structure mean a group or ring structure, which is organic, i.e. is a carbon compound radical with the exception of radicals of non-hydrogen chalcogenides and their derivatives, salt-like and metallic carbides and metal carbonyls. A hydroaromatic derivative means a compound of similar ring structure but with the benzene rings partially or completely hydrogenated.

In the $\eta^5$ ligand according to formula (I), $R_1$–$R_6$ are preferably hydrogen and, independently, one or two of $R_7$–$R_9$ are each independently a $C_1$–$C_{20}$ hydrocarbyl, preferably a $C_5$–$C_{20}$ hydrocarbyl, most preferably phenyl. Said ligand having the formula (I) is preferably a substituted or unsubstituted cyclopent[a]acenaphthtadienyl ligand or a hydroaromatic derivative thereof, preferably a 7,9-diphenylcyclopent[a]acenaphthtadienyl ligand.

It is advantageous, if in the metallocene compound, the number of said $\eta^5$ ligands comprising at least four fused rings is 1 or 2.

The metallocene compound according to the invention can in addition to said $\eta^5$ ligands comprising at least four fused rings have other ligands, as well. These other ligands can be $\eta^5$ ligands comprising less than four fused rings, σ (-bound) ligands, ligands of ionic nature and bridge ligands. A bridge is a bivalent atom or group which is bound to two moieties selected from the transition metall central atom and the ligands of the metallocene compound.

According to one embodiment of the invention, all $\eta^5$ ligands of the metallocene compound are $\eta^5$ ligands comprising at least four fused rings. The compound may, of course, also have other, non-$\eta^5$ ligands such as halogens, hydrocarbyls and heteroatom bridge structures. According to another embodiment, the metallocene compound comprises a $\eta^5$ ligand having less than four fused rings such as two fused rings, like substituted or unsubstituted, iso- or heterocyclic indene or tetrahydroindene, or three fused rings, like substituted or unsubstituted, iso- or heterocyclic fluorene or octahydrofluorene. The number of said $\eta^5$ ligands having less than four fused rings is preferably 0 or 1.

As was said above, the claimed metallocene compound may have other than $\eta^5$ ligands. According to an embodiment of the invention, the metallocene compound has at least one non-$\eta^5$ ligand, which is one of hydrogen, a halogen, an organic group having from 1 to 10 carbon atoms or an organic group forming together with said transition metal a metallocyclic ring structure having from 4 to 20 carbon atoms. Preferably, the non-$\eta^5$ ligand is one of a hydrocarbyl having from 1 to 10 carbon atoms or a halogen, most preferably one of methyl or chlorine. The number of said non-$\eta^5$ ligands is preferably 1–3, more preferably 1 or 2, most preferably 2.

According to an embodiment of the invention, the claimed metallocene compound may have at least one bridge, which is a bivalent atom or a bivalent organic group having from 1 to 20 carbon atoms and which connects two of said $\eta^5$ ligands or one of said $\eta^5$ ligands and said transition metal. The bridge is preferably attached to the $\eta^5$ bound cyclopentadiene ring of one or two of said $\eta^5$ ligands.

According to one embodiment of the invention, said bridge is a bridge between two of said $\eta^5$ ligands. Being so, it is preferably a silylene bridge having two organic substituents with 1 to 10 carbon atoms, e.g. two methyls, or an alkylene bridge having from 1 to 20 carbon atoms, e.g. ethylene. Most preferably, the bridge between two of said $\eta^5$ ligands is an aromatically substituted alkylene bridge, most preferably a phenylethylene bridge.

According to another embodiment of the invention, said bridge is bridge between one of said $\eta^5$ ligands and said transition metal. Being so, it preferably comprises, connected in succession, a first bivalent group of the formula —NR—, —PR—, —O—, or —S—, and a second bivalent hydrocarbylene group having 1–20 carbon atoms, said first bivalent group most preferably being bound to said transition metal.

The number of said bridges between two of said $\eta^5$ ligands or one of said $\eta^5$ ligands and said transition metal is preferably 0, 1 or 2, more preferably 0 or 1, most preferably 1.

According to a conclusive preferable embodiment of the present invention, said metallocene compound has 1 or 2 of said $\eta^5$ ligands having at least four used rings, 0 or 1 of said $\eta^5$ ligands having less than four fused rings, 1, 2 or 3 of said non-$\eta^5$ ligands and 0 or 1 of said bridges.

Advantageously the claimed metallocene compound has the formula (II)

$$(ACp)_g(BCp)_h M''X_iY_jZ_k \qquad (II)$$

wherein: ACp or each same or different ACp is an $\eta^5$ ligand of the formula (I)

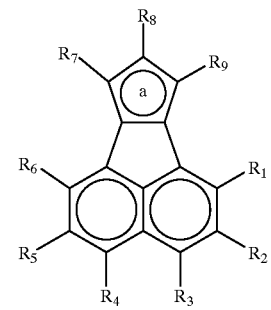

(I)

wherein each same or different of groups $R_1$–$R_9$ is one of hydrogen, a halogen, an organic group having from 1 to 20 carbon atoms or at least one pair of adjacent groups from $R_1$–$R_9$ form together an organic ring structure having from 5 to 20 carbon atoms, one of $R_7$ to $R_9$ being optionally replaced by a bridge Z to another $\eta^5$ ligand ACp or BCp, and a indicates an $\eta^5$ bound cyclopentadienyl ring, or a hydroaromatic derivative thereof; BCp or each same or different BCp is one of a mono- or polysubstituted, fused or non-fused, iso-(homo-) or heterocyclic, indenyl $\eta^5$ ligand or fluorenyl $\eta^5$ ligand, or a hydroaromatic derivative thereof; M is a transition metal of one of Groups 4 and 5 of the Periodic Table (IUPAC 1990) and bound to said ligand or ligands ACp and BCp in at least a $\eta^5$ bonding mode; X or each same or different X is bound to M and is one of hydrogen, a halogen, an organic group having from 1 to 20 carbon atoms or two X form together with said M a metallocyclic ring structure having from 4 to 20 carbon atoms; Y is a bridge atom or bridge organic group having from 1 to 20 carbon atoms between one of said ligands ACp or BCp and said transition metal M; Z is a bridge atom or bridge group between two of said ACp or BCp ligands; g is 1–4; h is 0–3; i is 1–4; j is 0–2; k is 0–2; g+h>1 and n=valence of M=g+h+i+j.

A particularly advantageous metallocene compound of the invention has the formula (IIIa) or (IIIb):

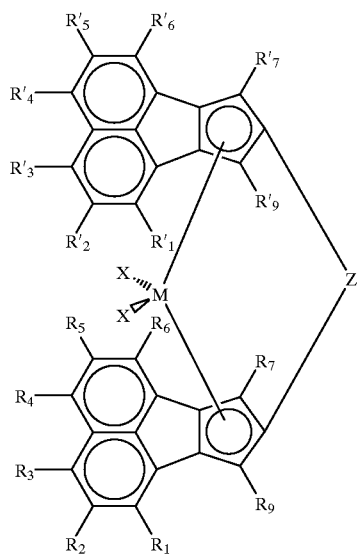

(IIIa)

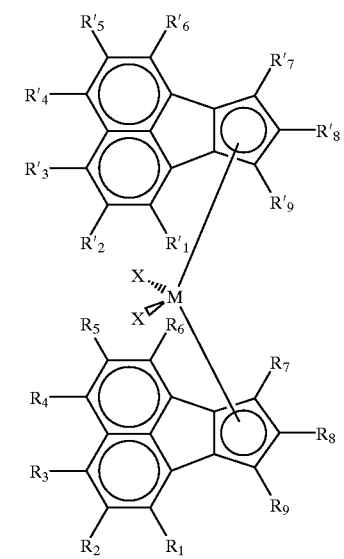

(IIIb)

wherein: each same or different of $R_1$ to $R_9$ and $R_1'$ to $R_9'$ is one of a hydrogen atom, a halogen atom, a hydrocarbon group having 1 to 20 carbon atoms or at least one pair of adjacent groups of $R_1$–$R_9$ form together an organic ring structure having from 5 to 20 carbon atoms; M is a four-valent transition metal of Group 4 of the Periodic Table (IUPAC 1990); each same or different X is bound to M and is one of hydrogen, a halogen, an organic group having from 1 to 20 carbon atoms or two X form together with said M a metallocyclic ring structure having from 4 to 20 carbon atoms; and bridge Z is a bivalent atom or bivalent group.

In the metallocene compounds of formulas (IIIa) and (IIIb), the four-valent transition metal is preferably zirconium or hafnium, most preferably zirconium. X is preferably a halogen, most preferably chlorine, or preferably an alkyl having from 1 to 4 carbon atoms, most preferably methyl. At least one of $R_7$, $R_7'$, $R_9$, and $R_9'$ is advantageously a substituted or unsubstituted cyclic organic group having from 5 to 20 carbon atoms, most advantageously a substituted or unsubstituted aromatic group, most preferably a phenyl group. According to an embodiment, $R_7$, $R_7'$, $R_9$, and $R_9'$ are phenyl groups and, preferably, groups $R_1$ to $R_6$ and $R_1'$ to $R_6'$ are hydrogens.

The bridge Z of the metallocene compounds of formulas (IIIa) and (IIIb) is according to an embodiment a silylene bridge having two organic substituents with 1 to 10 carbon atoms, for example two methyl susbtituents, or an alkylene bridge having from 1 to 20 carbon atoms, e.g. an ethylene bridge. Most preferably, the bridge Z is an alkylene bridge substituted with a substituted or unsubstituted cyclic organic group having from 5 to 20 carbon atoms, preferably a substituted or unsubstituted aromatic group, most preferably a phenyl group. Advantageously, the bridge Z is phenyl ethylene.

The metallocene compounds of formulas (IIIa) and (IIIb) are, for example, {[1-(7,9-diphenylcyclopent[a]acenaphthadienyl)-1-phenyl-2-(7,9-diphenylcyclopent[a]acenaphthadienyl)]ethane}zirconium dichloride having the formula (IV):

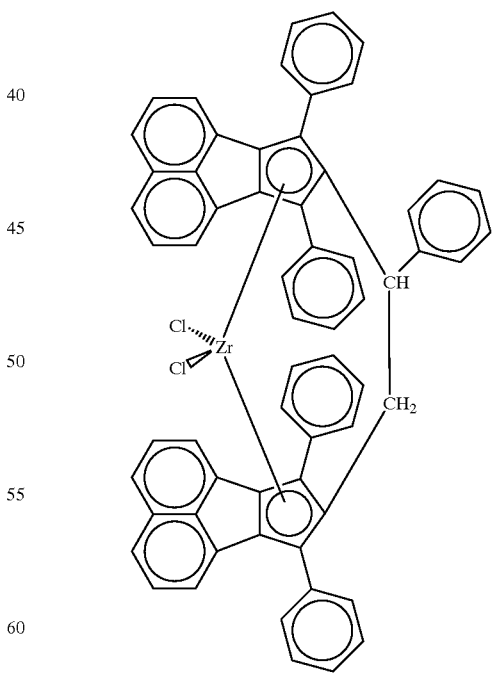

(IV)

The metallocene compounds of formulas (IIa) and (IIb) may also advantageously be {[1-(7,9-diphenylcyclopent[a]acenaphthadienyl)-1-phenyl-2-fluorenyl]ethane}zirconium dichloride having the formula (V):

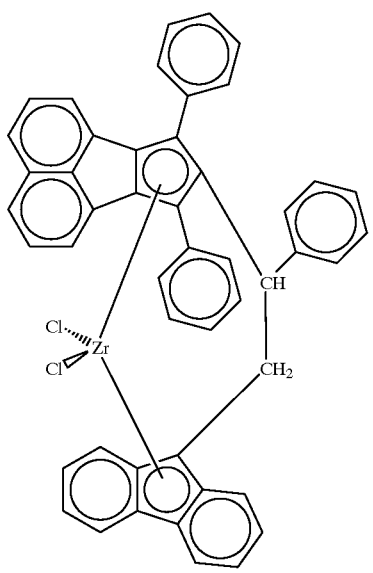

(V)

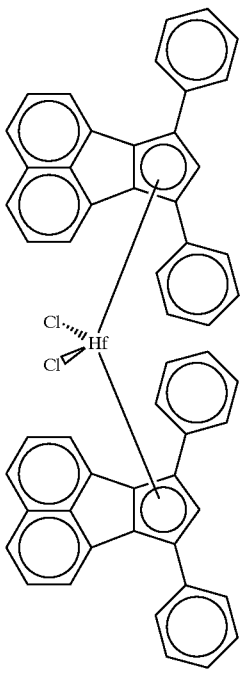

(VII)

The metallocene compounds of formulas (IIIa) and (IIIb) may also advantageously be [bis(7,9-diphenylcyclopent[a]acenaphthadienyl)]zirconium dichloride having the formula (VI):

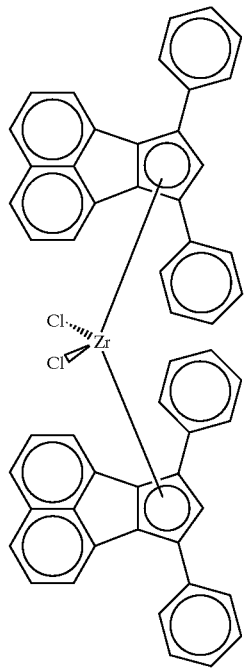

(VI)

The metallocene compounds of formulas (IIIa) and (IIIb) may further advantageously be [bis(7,9-diphenylcyclopent[a]acenaphthadienyl)]hafnium dichloride having the formula (VII):

The present invention also relates to a process for the preparation of a metallocene of said metallocene compound. In the process there are the steps of.

(a) forming of an alkali metal salt of at least one cyclopentadiene derivative comprising at least four fused rings including a cyclopentadiene ring, (b) forming said metallocene by reacting said alkali metal salt with a transition metal halide comprising at least two halogens.

If the metallocene compound comprises a substituted or unsubstituted ethylene bridge between two $\eta^5$ ligands, said metallocene is preferably prepared according to the following reaction scheme:

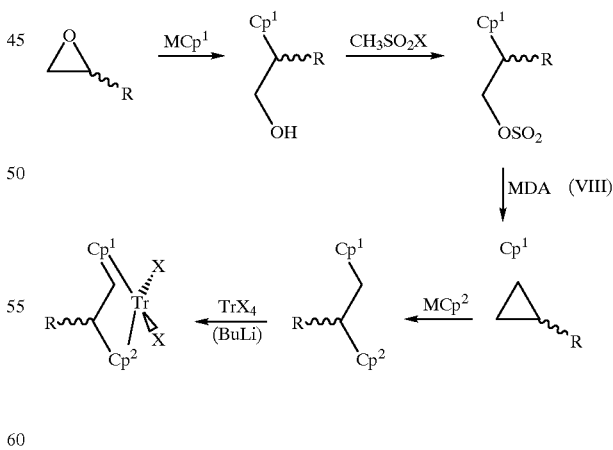

wherein each M is independently an alkali metal, preferably lithium, R is hydrogen or a hydrocarbyl group having 1–20 carbon atoms, preferably phenyl, each X is independently a halogen, preferably chlorine, $Cp^1$ is a cyclopentadiene derivative comprising at least four fused rings including a cyclopentadiene ring, preferably 7,9-diphenylcyclopent[a]

acenaphthadienyl and $Cp^2$ is the same or different $Cp^1$ or a cyclopentadiene derivative comprising less than four, preferably two or three fused rings including a cyclopentadiene ring, preferably one of 7,9-diphenylcyclopent[a] acenaphthadienyl, indenyl, tetrahydroindenyl, fluorenyl and octahydrofluorenyl, preferably 7,9-diphenylcyclopent[a] acenaphthadienyl or fluorenyl, MDA is an alkalimetal salt of a dialkyl amine, preferably a lithium salt of diisopropyl amine, and Tr is a transition metal, preferably Zr or Hf In addition to said metallocene compound and its preparation process, the invention also relates to an olefin polymerization catalyst composition, which comprises said metallocene compound and an activator thereof. The activator may be any compound in the art which activates metallocenes for polymerization, including alkylalumimum compounds, alkyl aluminoxanes such as methyl aluminoxane, tetraisobutyl aluminoxane (cage structure) and hexaisobutylaluminoxane (cage structure). It may also be a Lewis or protic acids such as $B(C_6H_5)_3$ or $[PhNMe_2H]^+B(C_6F_5)_4^-$, which generates cationic metallocenes with compatible non-coordinating anions in the presence or absence of alkylaluminium compounds.

Preferred activators of the claimed polymerization catalyst composition are alkyl aluminoxanes having one of the following formulas (IX and X):

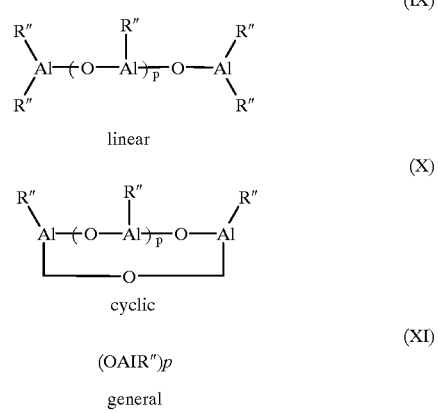

(IX) linear (X) cyclic (XI) $(OAlR'')p$ general wherein: each R" is the same or different and is an organic group having from 1 to 20 carbon atoms, preferably an alkyl group having from 1 to 10 carbon atoms; and p is an integer between 1 and 40.

A particularly preferred aluminoxane activator is methyl aluminoxane.

Particularly important is the claimed process for polymerizing at least one ethylenically unsaturated monomer. Such a monomer may be a monoethylenically unsaturated compound, e.g. an olefin such as ethene, propene, 1-butene, 1-pentene, 1-hexene, 1-heptene, 1-octene, 1-nonene, 1-decene, isobutene, 3-methyl-1-butene, 4-methyl-1-pentene, 4,4-dimethyl-1-pentene and vinylcyclohexane, a vinyl compound such as vinyl acetate, vinyl chloride, vinyl fluoride, a styrenic compound such as styrene, α-methyl styrene and vinyl styrene, an acrylic monomer such as methyl acrylate, methyl methacrylate and acrylonitrile. The monomer may also be a polyethylenically unsaturated compound such as 1,3-butadiene, isoprene, 2,3-dimethyl-1,3-butadiene and chloroprene, as well as dicyclopentadiene, 4-ethyl-2-norbornene and 1,4-hexadiene.

According to the invention, the monomer is polymerized in the presence of a metallocene compound described above and preferably in the presence of a catalyst composition (metallocene compound plus activator) as described above. Because the aim of the invention was to find a metallocene compound useful for the polymerization of ethene to high molecular weight polyethene, the process of polymerizing ethene to high molecular weight polyethene is particularly important and preferred. By high molecular weight polyethene is meant polyethene having a molecular weight of about 200,000 g/mol to about 2,000,000 g/mol, preferably about 1,000,000 g/mol.

Another advantage of the claimed metallocene compound and catalyst composition is that they can be used to prepare vinyl terminated polypropene molecules. Without limiting the scope of protection, vinyl termination is believed to take place through β-elimination of methyl at the active sites of the catalyst composition. The vinyl terminal groups of the polypropene molecules are reactive and are during continuous polymerization or separate post-polymerization attached to the polypropene macromolecular chains, whereby long-chain branched polypropene is formed. Such a preparation of long-chain branched polypropene using said metallocene or said catalyst composition is also claimed.

EXAMPLES

In the present invention cyclopentadienyl moieties of zirconocene(IV) dichlorides were modified with large and sterically demanding acenapthtyl derivatives in order to use them for α-olefine polymerization. The 7,9-diphenylcyclopent[a]-acenaphthadiene (ACp) and its, spiro derivative spiro(2-phenylcyclopropane)-1,1'-(7,9-diphenylcyclopent[a]acenaphthadiene was prepared according to Rieger, B., Repo, T., Jany, Gr., Polym. Bull, 35 (1955) 87, 88, included here in by reference.

The preparation of the ligands and new complexes, {[1-(7,9-diphenylcyclopent[a]acenaphthadienyl)-1-phenyl-2-(7,9-diphenylcyclopent[a]acenaphthadienyl)]ethane}zirconium dichloride (1), {[1-(7,9-diphenylcyclopent[a]acenaphthadienyl)-1-phenyl-2-fluorenyl]ethane}zirconium dichloride (2) and [bis(7,9-diphenylcyclopent[a]acenaphthadienyl)]zirconium (3) and hafnium (4) dichloride, is detailed described in experimental section below. The complexes 1–3 were further characterized by x-ray measurements. The ethylene and propene polymerization behaviour of the complexes 1–4, when activated with MAO, was studied and results are summarized in form of table. From this series the complex 2 turned out to be the most active and it produces polyethylene with high molecular weight (see Table, tests 29–33.).

Polymer Properties

Polypropene: All the complexes presented in this invention produced short chain atactic polypropylenes. What is interesting in these polymers is, that according to $^1H$ NMR, chain termination happens via β-methyl elimnnation. This leads to vinyl terminated polymers, which can be further polymerized and thus it might be possible to utilize these polymers as macromonomers in preparation of branched polymers.

Polythylene: Depending on the catalysts system and polymerization conditions used, molecular weights of polyethylenes varied from 63,000 to 1,111,000 to g/mol. The fluorenyl/ACp zirconium complex shows the highest activity and also highest molecular weights. Molecular weight distributions of the zirconium complexes are around 2, indicating single site character of the catalyst systems used.

Experimental Section

Reactions and manipulations with organometallic compounds were carried out under inert argon or nitrogen atmosphere using standard syringe or Schlenk-techniques. Solvents were dried and purified under argon with standard methods. Zirconium and hafinium tetrachloride (Aldrich) were used without further purification. The preparation of 7,9-diphenylcyclopent[a]acenaphthadiene (ACp) and spiro{spiro[(2-phenylcyclopropane)-1,1'-(7,9-diphenylcyclopent[a]acenaphthadiene)]} (1) were carried out as described earlier. The $^1$H and $^{13}$C NMR spectra were measured on a Varian Gemini 200 MHz NMR spectrometer Me$_4$Si as internal standard. The FAB mass spectra were recorded on a JEOL SX 102 mass spectrometer and EI-mass spectra on a JEOL JMS-SX 102 mass spectrometer at 70 eV.
Polymerization Procedure.

Methylaluminoxane (MAO, 10 wt. % solution in toluene, M=800 g/mol, Al=5.3 wt. %) was from Witco GmbH. Ethylene (grade 3.5 from AGA) and propene (grade 2.8 from AGA) were purified by passing them through columns filled with molecular sieves, CuO and Al$_2$O. Toluene (GR grade from Merck) was distilled from Na/benzophenone and stored under nitrogen.

Polymerizations were carried out in toluene in a 0.5 dm$^3$ stainless steel reactor equipped with a propeller-like stirrer. The shrnng speed was 400 rpm. Temperature was 30–90° C. and partial pressure of monomer 1.4–5.7 bar.

Toluene (300 cm$^3$) was introduced to the nitrogen-purged reactor. The cocatalyst solution was added to the reactor under nitrogen pressure. The reactor temperature was controlled by circulating water in the reactor jacket. At the polymerization temperature the monomer feed was started. After the equilibrium was reached, polymerization was initiated by pumping the toluene solution of the catalyst into the reactor. During polymerization the partial pressure of monomer was maintained constant with an electronic pressure controller.

After the polymerization time the reactor was degassed. The polymer was separated from solution with methanol containing a small amount of hydrochloric acid. The product was washed with methanol and dried under vacuum.
Polymer Characterization A Waters 150-C ALC/GPC operating at 140° C. end equipped with three Polymer Laboratories PLgel 10 μm columns was used to determinate the molecular weights and molecular weight distributions of the polymers. Solvent 1,2,4-trichlorobenzene was applied at a flow rate 1.0 cm$^3$/min. The columns were calibrated with narrow molecular weight distribution polystyrenes and then with polypropylene or linear low density polyethylene standards.

The melting temperatures of polyethylenes were recorded with Mettler Toledo DSC82le differential scanning calorimeter. The melting endotherms were measured upon reheating the polymer sample to 160° C. at heating rate of 10° C./min.

Synthesis of [1-(7,9-diphenylcyclopent[a]
acenaphthadienyl)-1-phenyl-2-(7,9-
diphenylcyclopent[a]acenaphthadienyl)]ethane (2)

7,9-diphenylcyclopent[a]acenaphthadiene (ACp) (4.99 g, 14.6 mmole) was dissolved into 100 ml abs. diethyl ether. The solution was cooled down to 0° C. and n-butyllithium (9.1 ml, 14.6 mmole) was added dropwise. The reaction mixture was stirred one hour over ice bath and after this the diethyl ether was removed. This dry yellow lithium salt was dissolved to 100 ml of abs. DMF and violet/dark red mixture was cooled down to –10° C. Spiro[(2-phenylcyclopropane-1,1'-(7,9-diphenylcyclopent[a]acenaphthadiene)] (5.4 g, 12.2 mmole) was then added and this reaction mixture was then stirred 48 hours. DMF was removed and solid residue was washed with 200 ml of toluene. Collected organic phases were dried over Na$_2$SO$_4$. The ligand was cleaned up by column chromatography using toluene as an eluent. For the frrther purification the ligand was recrystalized from toluene as yellow crystals (3.1 g, 3.9 mmole, 32%), mp. 257° C. $^1$H NMR (CDCl$_3$): δ 1.89–2.15 (m, 2H), 3.10–3.25 (m, 1H), 4.37–4.42 (m, 1H), 4.50 (d, J=3.34 Hz, 1H), 6.83–7.92 (m, 37H). FDMS: 786 (M$^+$). Anal. Cal. for C$_{62}$H$_{42}$, C, 94.62; H, 5.38. Found C, 94.84; H, 5.28.

Synthesis of {[1-(7,9-diphenylcyclopent[a]
acenaphthadienyl)-1-phenyl-2-(7,9-
diphenylcyclopent[a]acenaphthadienyl)]
ethane}zirconium dichloride (4)

Ligand (bisACp) (1.9 g, 2.4 mmole) was diluted in 20 ml abs. THF. Solution was cooled down to –78° C. After this n-butyllithium (3.0 ml, 4.8 mmole) was added dropwise. The color of the solution turned dark red. After 10 minutes the reaction mixture was allowed to reach slowly ambient temperature and stirring was continued 30 min at room temperature. Solution was cooled down to –78° C. again and ZrCl$_4$·(THF)$_2$ (0.91 g, 2.4 mmole) was added. Reaction mixture was then slowly heated up to 60–65° C. and stirred at this temperature three hours. Solution turned to yellow. THF was then removed and abs. toluene 35 ml was added and heated few minutes with hot water bath. Precipitation which was left was then filtered off. To this solution 10 ml abs. n-hexane was added and precipitation was filtered again. After this firther addition of n-hexane (partial crystallization) gave yellow solid powder (318 mg, 0.34 mmole, 14%). $^1$H NMR (CDCl$_3$): δ 4.14–4.48 (m, 2H), 5.46–5.56 (m, 1H), 6.62–8.32 (M, 37H). In the FAB-MS spectrum of 4, parent ions of composition C$_{62}$H$_{40}$ZrCl$_2$$^+$ were observed in the appropriate isotope ratios at m/e=946.7 (M$^+$) and 911.7 (M$^+$-Cl). Anal. Cal. for C$_{62}$H$_{40}$ZrCl$_2$, C, 78.70; H, 4.26; Cl 7.49. Found C, 78.72; H, 5.44; Cl, 7.31.

Synthesis of [bis(7,9-diphenylcyclopent[a]
acenaphthadienyl)]zirconium dichloride (5)

ACp (4.08 g, 11.9 mmol) was dissolved in 70 ml tetrahydrofurane (THF) and cooled down to –78° C. n-Butyl lithium (7.5 ml, 1.6 M, 11.9 mmol) was dropped slowly to solution. The reaction mixture was then allowed to reach room temperature and strirred one hour. THF was then removed and dry solid powder was cooled to –78° C. Precooled CH$_2$Cl$_2$ (–78° C.) (40 ml) was transferred into the Schlenk tube and ZrCl$_4$ (1.39 g, 6.0 mmol) was added. Reaction was allowed to reach slowly ambient temperature and the stirring was continuated overnight Greenish yellow suspension was then filterated through Celite and the volume was reduced to one third. Yellow solid powder (0.95 g, 1.1 mmol) was isolated with 18% yield. $^1$H NMR (CDCl$_3$): δ 6.37 (s, 2H), 7.10–7.85 (m, 32H). FAB-MS: 845 [M$^+$], 810 [M$^+$-Cl].

Synthesis of bis(7,9-diphenylcyclopent[a]
acenaphthadienyl)]hafnium dichloride (6)

Title complex was prepared similarly as the zirconium analog. $^1$H NMR (CDCl$_3$): δ 6.28 (s, 2H), 7.19–8.14 (m, 32H) FAB-MS: 932 [M$^+$], 897 [M$^+$-Cl], 591 [M$^+$-ACp]. HRMS (FAB) calculated for C$_{54}$H$_{34}$HfCl$_2$ ($^{180}$Hf) 932.1500 found 932.1553.

Synthesis of [1-(7,9-diphenylcyclopent[a]
acenaphthadienyl)-1-phenyl-2-(fluorenyl)]ethane (3). Fluorene (1.35 g, 8.1 mmol) was dissolved into THF and treated dropwise with n-butyllitlium (1.6 M, 5.1 ml, 8.1 mmol) at –78° C. The reaction mixture was then stirred one hour at room temperature. Spiro[(2-phenylcyclopropane)-1,1'-(7,9- diphenylcyclopent[a]acenaphthadiene)] (3.6 g, 8.1 mmol) dissolved into 50 ml THF was added dropwise to the solution of lithium salt at 0° C. After stining overnight at ambient temperature the solution neutralized by the addition of a saturated aqueous solution of NH$_4$Cl. The agueous phase was extracted with toluene (2×100 ml) and the collected organic phases were dried (Na$_2$SO$_4$) and the solvent was distilled off. The brownish oily raw material was purified by column cromatography (eluent: mixture of toluene/hexane 1:2) and orange-yellow powder (3.1 g, 5.1 mmol) was obtained with 58% yield. $^1$H NMR (CDCl$_3$): δ EI-MS: 610 (M$^+$). HRMS(EI) Calcd. for C$_{48}$H$_{34}$ 610.2660. Found 610.2662.

Synthesis of {[1-(7,9-diphenylcyclopent[a] acenaphthadienyl)-1-phenyl-2-fluorenyl] ethane}zirconium dichloride (7)

Compound 3 (2.9 g, 4.8 mmol) was dissolved in diethylether (50 ml) and treated dropwise with n-butyllithium (1.6 M, 5.9 ml, 9.5 mmol) at −78° C. After stirring one hour at room temperature the solvent was removed in vacuo and dilithiosalt was dissolved in precooled methylenechloride (−78° C.). ZrCl$_4$ (1.12 g, 4.8 mmol) was added and reaction mixture was allowed slowly to reach room temperature. Reaction mixture was stirred overnight and then heated to 50° C. for half an hour. Methylene chloride was then removed in vacuo and yellowish raw product was dissolved in toluene (40 ml). Addition of hexane (2×40 ml) dropped out yellow solid, which was removed by filtration. From the clear solution was obtained a red product (0.66 g, 0.8 mmol) with 18% yield by crystallization at −20° C. Crystallized clear red solution was then transferred into the refrigerator and left standing overnight. Single crystals suitable for x-ray measurement were obtained from the concentrated CHCl$_3$ solution at ambient temperature.

FAB-MS: 771 (M$^+$), (M$^+$-Cl) and 609 [ligandH$^+$].

TABLE

Polymerizations of propylene and ethylene with metallocene catalysts containing ACp ligands  
Catalysts ACp$_2$ZrCl$_2$ and ACp$_2$HfCl$_2$  
Cocatalyst MAO (10 w-% in toluene)  
Medium: toluene (300 ml)

| Run | Monomer | Catalyst | $n_{cat}$ μmol | Al/Zr mol/mol | $T_p$ °C | $p_{monom.}$ bar | $t_p$ min | Yield g | A kg P/(mol Zr*h) | $M_w$ g/mol | $M_w$/M | $T_m$ °C |
|---|---|---|---|---|---|---|---|---|---|---|---|---|
| 1 | propylene | ACp$_2$ZrCl$_2$ | 6.0 | 2000 | 30 | 1.4 | 60 | 0.08 | 13 | 8700 | 1.49 | — |
| 2 | propylene | ACp$_2$ZrCl$_2$ | 6.0 | 2000 | 50 | 2.0 | 60 | traces | — | — | — | — |
| 3 | propylene | ACp$_2$ZrCl$_2$ | 6.0 | 2000 | 70 | 2.9 | 60 | none | — | — | — | — |
| 4 | propylene | ACp$_2$ZrCl$_2$ | 6.0 | 2000 | 80 | 3.3 | 60 | none | — | — | — | — |
| 5 | propylene | ACp$_2$ZrCl$_2$ | 6.0 | 2000 | 50 | 4.6 | 60 | 0.21 | 35 | 5900 | 1.43 | — |
| 6 | propylene | ACp$_2$ZrCl$_2$ | 6.0 | 2000 | 50 | 5.7 | 60 | 0.32 | 53 | 6900 | 1.50 | — |
| 7 | propylene | ACp$_2$ZrCl$_2$ | 9.0 | 4000 | 50 | 4.6 | 60 | 0.32 | 36 | 6900 | 1.33 | — |
| 8 | ethylene | ACp$_2$ZrCl$_2$ | 3.0 | 2000 | 30 | 2.8 | 30 | 0.66 | 440 | 630 400 | 2.82 | 138.3 |
| 9 | ethylene | ACp$_2$ZrCl$_2$ | 3.0 | 2000 | 50 | 3.8 | 30 | 1.76 | 1173 | 281 500 | 2.07 | 137.7 |
| 10 | ethylene | ACp$_2$ZrCl$_2$ | 3.0 | 2000 | 60 | 4.2 | 30 | 1.83 | 1220 | 198 000 | 2.08 | 135.3 |
| 11 | ethylene | ACp$_2$ZrCl$_2$ | 3.0 | 2000 | 70 | 4.6 | 30 | 1.89 | 1260 | 181 200 | 2.84 | 135.2 |
| 12 | ethylene | ACp$_2$ZrCl$_2$ | 3.0 | 2000 | 80 | 5.0 | 30 | 1.77 | 1180 | 160 100 | 2.65 | 134.4 |
| 13 | ethylene | ACp$_2$ZrCl$_2$ | 3.0 | 2000 | 90 | 5.4 | 30 | 1.63 | 1087 | 152 900 | 2.79 | 135.9 |
| 14 | ethylene | ACp$_2$ZrCl$_2$ | 6.0 | 2000 | 50 | 3.8 | 30 | 3.36 | 1120 | 246 800 | 2.35 | 138.1 |

| Run | Monomer | Catalyst | $n_{cat}$ μmol | Al/Hf mol/mol | $T_p$ °C | $p_{monom.}$ bar | $t_p$ min | Yield g | A kg P/(mol Hf*h) | $M_w$ g/mol | $M_w$/M | $T_m$ °C |
|---|---|---|---|---|---|---|---|---|---|---|---|---|
| 15 | ethylene | ACp$_2$HfCl$_2$ | 3.0 | 3000 | 50 | 3.8 | 30 | 0.27 | 180 | 101 500 | 6.38 | 134.4 |
| 16 | ethylene | ACp$_2$HfCl$_2$ | 3.0 | 2000 | 70 | 4.6 | 30 | 0.88 | 587 | 63 700 | 6.78 | 132.6 |

| Run | Monomer | Catalyst | $n_{cat}$ μmol | Al/Zr mol/mol | $T_p$ °C | $p_{monom.}$ bar | $t_p$ min | Yield g | A kg P/(mol Zr*h) | $M_w$ g/mol | $M_w$/M | $T_m$ °C |
|---|---|---|---|---|---|---|---|---|---|---|---|---|
| 17 | propylene | PhEtACp$_2$ZrCl$_2$ | 6.0 | 2000 | 50 | 2.0 | 60 | traces | — | — | — | — |
| 18 | propylene | PhEtACp$_2$ZrCl$_2$ | 6.0 | 2000 | 70 | 2.9 | 60 | traces | — | — | — | — |
| 19 | propylene | PhEtACp$_2$ZrCl$_2$ | 6.0 | 2000 | 80 | 3.3 | 60 | traces | — | — | — | — |
| 20 | propylene | PhEtACp$_2$ZrCl$_2$ | 6.0 | 2000 | 50 | 4.6 | 60 | 1.8 | 300 | 9300 | 1.78 | — |
| 21 | propylene | PhEtACp$_2$ZrCl$_2$ | 6.0 | 2000 | 50 | 5.7 | 60 | 2.4 | 400 | 11 100 | 1.82 | — |
| 22 | ethylene | PhEtACp$_2$ZrCl$_2$ | 3.0 | 2000 | 50 | 3.8 | 30 | 1.22 | 813 | 183 200 | 2.40 | 136.8 |
| 23 | ethylene | PhEtACp$_2$ZrCl$_2$ | 3.0 | 2000 | 70 | 4.6 | 30 | 1.20 | 800 | 91 300 | 2.04 | 134.0 |

| Run | Monomer | Catalyst | $n_{cat}$ μmol | Al/Zr mol/mo | $T_p$ °C | $p_{monom.}$ bar | $t_p$ min | Yield g | A kg P/(mol Zr*h) | $M_w$ g/mol | $M_w$/M | $T_m$ °C |
|---|---|---|---|---|---|---|---|---|---|---|---|---|
| 24 | propylene | PhEtACpFluZrCl$_2$ | 6.0 | 2000 | 30 | 1.4 | 60 | 2.4 | 400 | 12 800 | 1.85 | — |
| 25 | propylene | PhEtACpFluZrCl$_2$ | 6.0 | 2000 | 50 | 2.0 | 60 | 4.5 | 750 | 4000 | 1.68 | — |
| 26 | propylene | PhEtACpFluZrCl$_2$ | 6.0 | 2000 | 70 | 2.9 | 60 | 2.1 | 350 | 1800 | 1.32 | — |
| 27 | propylene | PhEtACpFluZrCl$_2$ | 6.0 | 2000 | 50 | 4.6 | 60 | 14.9 | 2483 | 8500 | 1.83 | — |
| 28 | propylene | PhEtACpFluZrCl$_2$ | 6.0 | 2000 | 50 | 5.7 | 60 | 23.1 | 3850 | 10 300 | 1.87 | — |
| 29 | ethylene | PhEtACpFluZrCl$_2$ | 3.0 | 2000 | 50 | 3.8 | 10 | 4.28 | 8560 | 486 100 | 2.54 | 136.3 |
| 30 | ethylene | PhEtACpFluZrCl$_2$ | 0.5 | 2000 | 50 | 3.8 | 30 | 0.37 | 1480 | not deter. | | 135.5 |
| 31 | ethylene | PhEtACpFluZrCl$_2$ | 2.0 | 2000 | 30 | 2.8 | 15 | 4.13 | 8260 | 1 111 000 | 1.84 | 134.1 |
| 32 | ethylene | PhEtACpFluZrCl$_2$ | 2.0 | 2000 | 50 | 3.8 | 15 | 7.62 | 15 240 | 801 700 | 2.75 | 134.7 |
| 33 | ethylene | PhEtACpFluZrCl$_2$ | 2.0 | 2000 | 70 | 4.6 | 15 | 5.91 | 11 820 | 186 500 | 3.02 | 136.5 |

What is claimed is:

1. A metallocene compound of a transition metal, characterized in that at least one of its η⁵ ligands has the formula (I):

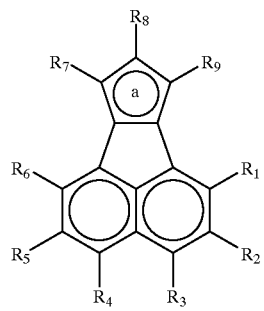

wherein each same or different of groups $R_1$–$R_9$ is one of hydrogen, a halogen and an organic group having from 1 to 20 carbon atoms, or at least one pair of adjacent groups from $R_1$–$R_9$ form together an organic ring structure having from 5 to 20 carbon atoms, one of $R_7$–$R_9$ being optionally replaced by a bridge to another η⁵ ligand, and a indicates the η⁵ bound cyclopentadienyl ring of said η⁵ ligand comprising at least four fused rings; or is a hydroaromatic derivative ligand thereof, and that the sum of fused rings in all of its η⁵ ligands is at least 6.

2. A metallocene compound according to claim 1, characterized in that it is based on a transition metal of Group 4 or 5 of the Periodic Table.

3. A metallocene compound according to claim 1, characterized in that $R_1$–$R_6$ are hydrogens and one or two of $R_7$–$R_9$ are a $C_1$–$C_{20}$ hydrocarbyl.

4. A metallocene compound according to claim 3, characterized in that said ligand having the formula (I) is a substituted or unsubstituted cyclopent[a]acenaphthadienyl ligand or a hydroaromatic derivative ligand thereof.

5. A metallocene compound according to claim 1, characterized in that the number of said η⁵ ligands comprising at least four fused rings is 1 or 2.

6. A metallocene compound according to claim 1, characterized in that it comprises a η⁵ ligand having less than four fused rings, including the η⁵ bound cylopentadiene ring.

7. A metallocene compound according to claim 6, characterized in that the number of said η⁵ ligands having less than four fused rings is 0 or 1.

8. A metallocene compound according to claim 1, characterized in that it comprises at least one non-η⁵ ligand, which is one of hydrogen, a halogen, an organic group having from 1 to 10 carbon atoms or an organic group forming together with said transition metal a metallocyclic ring structure having from 4 to 20 carbon atoms.

9. A metallocene compound according to claim 8, characterized in that said non-η⁵ ligand is one of a hydrocarbyl having from 1 to 10 carbon atoms or a halogen.

10. A metallocene compound according to claim 9, characterized in that the number of said non-η⁵ ligands is 1–3.

11. A metallocene compound according to claim 1, characterized in that it has at least one bridge, which is a bivalent atom or a bivalent organic group having from 1 to 20 carbon atoms and which connects two of said η⁵ ligands or one of said η⁵ ligands and said transition metal.

12. A metallocene compound according to claim 11, characterized in that said bridge is attached to the η⁵ bound cyclopentadiene ring of one or two of said η⁵ ligands.

13. A metallocene compound according to claim 12, characterized in that said bridge is a bridge between two of said η⁵ ligands.

14. A metallocene compound according to claim 13, characterized in that said bridge between two of said η⁵ ligands is a silylene bridge having two organic substituents with 1 to 20 carbon atoms or an alkylene bridge having from 1 to 10 carbon atoms.

15. A metallocene compound according to claim 13, characterized in that said bridge is bridge between one of said η⁵ ligands and said transition metal.

16. A metallocene compound according to claim 15, characterized in that said bridge between one of said η⁵ ligands and said transition metal comprises, connected in succession, a first bivalent atom or group of the formula —NR—, —PR—, —O—, or —S—, wherein R is a hydrocarbyl group having 1 to 10 carbon atoms, and a second bivalent organic group having 1–20 carbon atoms.

17. A metallocene compound according to claim 12, characterized in that the number of said bridges is 0, 1 or 2.

18. A metallocene compound according to claim 12, characterized in that it has 1 or 2 of said η⁵ ligands, 1, 2 or 3 of said non-η⁵ ligands and 0 or 1 of said bridges.

19. A metallocene compound according to claim 1, characterized in that it has the formula (II)

wherein: ACp or each same or different ACp is a η⁵ ligand of the formula (I)

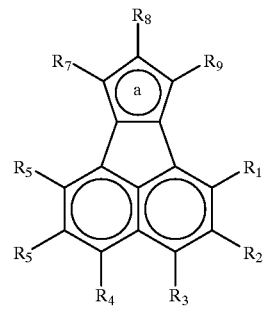

wherein each same or different of groups $R_1$–$R_9$ is one of hydrogen, a halogen, an organic group having from 1 to 20 carbon atoms or at least one pair of adjacent groups from $R_1$–$R_9$ form together an organic ring structure having from 5 to 20 carbon atoms, one of $R_7$ to $R_9$ being optionally replaced by a bridge Z to another η⁵ ligand ACp or BCp, and a indicates an η⁵ bound cyclopentadienyl ring, or a hydroaromatic derivative thereof; BCp or each same or different BCp is one of a mono- or polysubstituted, fused or non-fused, iso- or heterocyclic, indenyl ligand or fluorenyl η⁵ ligand, or a hydroaromatic derivative thereof; M is a transition metal of one of Groups 4 and 5 of the Periodic Table (IUPAC 1990) and bound to said ligand or ligands ACp and BCp in at least an η⁵ bonding mode; X or each same or different X is bound to M and is one of hydrogen, a halogen, an organic group having from 1 to 20 carbon atoms or two X form together with said M a metallocyclic ring structure having from 4 to 20 carbon atoms; Y is a bridge atom or bridge organic group having from 1 to 20 carbon atoms between one of said ACp or BCp ligands and said transition metal M; Z is a bridge atom or bridge group between two of said ACp or BCp ligands; g is 1–4; h is 0–3; i is 1–4; j is 0–2; k is 0–2; g+h≧1 and n=valence of M=g+h+i+j.

20. A metallocene compound according to claim 1, characterized in that it has the formula (IIIa) or (IIIb):

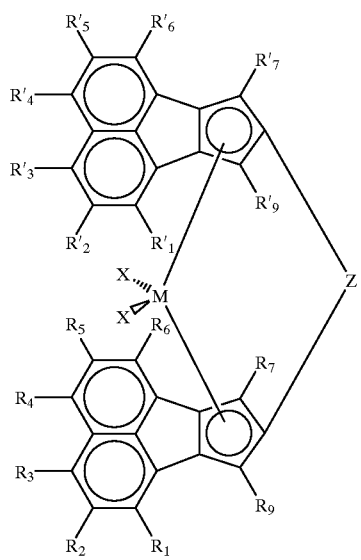

(IIIa)

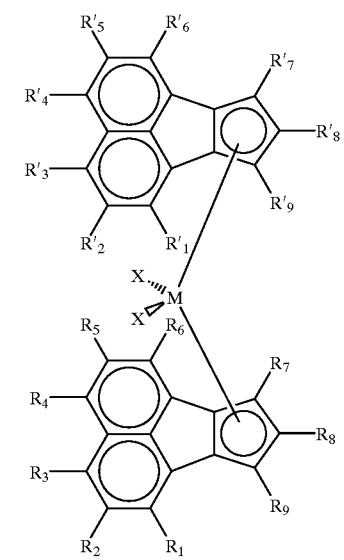

(IIIb)

wherein: each same or different of $R_1$ to $R_9$ and $R_1'$ to $R_9'$ is one of a hydrogen atom, a halogen atom, a hydrocarbon group having 1 to 20 carbon atoms or at least one pair of adjacent groups of $R_1$–$R_9$ form together an organic ring structure having from 5 to 20 carbon atoms; M is a four-valent transition metal of Group 4 of the Periodic Table (IUPAC 1990); each same or different X is bound to M and is one of hydrogen, a halogen, an organic group having from 1 to 20 carbon atoms or two X form together with said M a metallocyclic ring structure having from 4 to 20 carbon atoms; and bridge Z is a bivalent atom or bivalent group.

21. A metallocene compound according to claim 20, characterized in that M is zirconium or hafnium.

22. A metallocene compound according to claim 21, characterized in that X is a halogen or an alkyl having from 1 to 4 carbon atoms.

23. A metallocene comound according to claim 21, characterized in that at least one of $R_7$, $R_7'$, $R_9$ and $R_9'$, is a substituted or unsubstituted cyclic organic group having from 5 to 20 carbon atoms.

24. A metallocene compound according to claim 23, characterized in that $R_7$, $R_7'$, $R_9$ and $R_9'$, are phenyl groups and that, groups $R_1$ to $R_6$ and $R_1'$ to $R_6'$ are hydrogens.

25. A metallocene compound according to claim 21, characterized in that the bridge Z is a silylene bridge having two organic substituents with 1 to 10 carbon atoms or an alkylene bridge having from 1 to 20 carbon atoms.

26. A metallocene compound according to claim 21, characterized in that the bridge Z is an alkylene bridge substituted with a substituted or unsubstituted cyclic organic group having from 5 to 20 carbon atoms.

27. A metallocene compound according to claim 21, characterized in that the bridge Z is phenyl ethylene.

28. A metallocene compound according to claim 21, characterized in that it is {[1-(7,9-diphenylcyclopent[a]acenaphthadienyl)-1-phenyl-2-(7,9-diphenylcyclopent[a]acenaphthadienyl)]ethane} zirconium dichloride having the formula (IV):

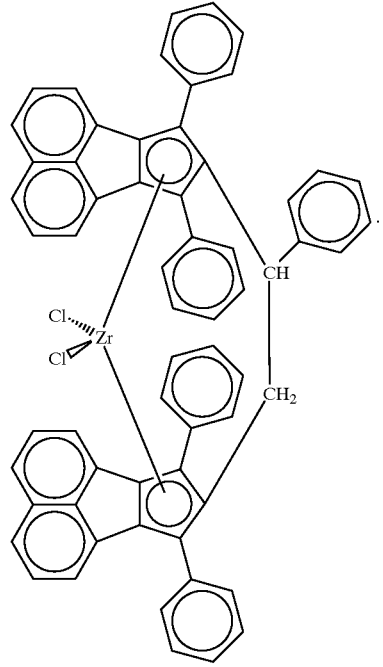

(IV)

29. A metallocene compound according to claim 21, characterized in that it is {[1-(7,9-diphenylcyclopent[a]acenaphthadienyl)-1-phenyl-2-fluorenyl]ethane} zirconium dichloride having the formula (V):

(V)

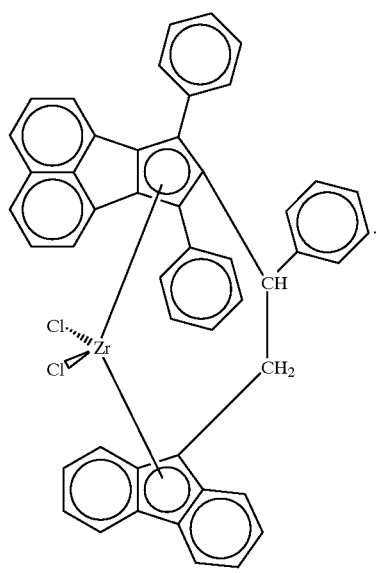

30. A metallocene compound according to claim 20, characterized in that it is [bis(7,9-diphenylcyclopent[a]acenaphthadienyl)] zirconium dichloride having the formula (VI):

(VI)

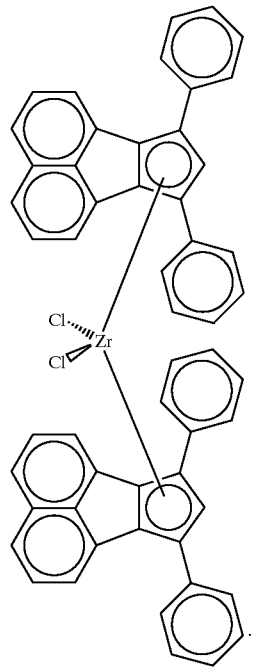

31. A metallocene compound according to claims 21, characterized in that it is [bis(7,9-diphenylcyclopent[a]acenaphthadienyl)] hafnium dichloride having the formula (VII):

(VII)

32. Process for the preparation of a metallocene compound according to claim 1, characterized in that it comprises
(a) forming of an alkali metal salt of at least one cyclopentadiene derivative comprising at least four fused rings including a cyclopentadiene ring,
(b) forming said metallocene by reacting said alkali metal salt with a transition metal halide comprising at least two halogens.

33. Process according to claim 32, characterized in that said metallocene compound is prepared according to the following reaction scheme:

wherein each M is independently an alkali metal, R is hydrogen or a hydrocarbyl group having 1–20 carbon atoms, each X is independently a halogen, $Cp^1$ is 7,9-diphenylcylopent acenaphthadienyl and $Cp^2$ is the same or different $Cp^1$ or a cyclopentadiene derivative comprising less than four fused rings, MDA is an alkalimetal salt of a dialkyl amine, and Tr is a transition metal.

34. An olefin polymerization catalyst composition, characterized in that it comprises a metallocene compound according to claim 1 and an activator.

35. An olefin polymerization catalyst composition according to claim 34, characterized in that said aluminoxane has one of the following formulas (V, IX, and XI):

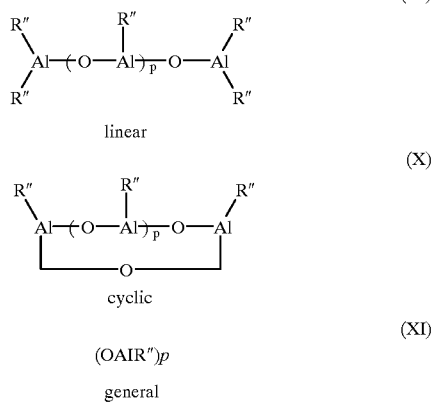

linear (IX)

cyclic (X)

(OAlR")p general (XI)

wherein: each R" is the same or different and is an organic group having from 1 to 20 carbon atoms, preferably an alkyl group having from 1 to 10 carbon atoms; and p is an integer between 1 and 40.

36. A catalyst composition according to claim 35, characterized in that said aluminoxane is methyl aluminoxane.

37. A process for polymerizing at least one ethylenically unsaturated monomer, characterized in that ethylenically unsaturated monomer is polymerized in the presence of a metallocene compound according to claim 1.

38. A process according to claim 37, characterized in that ethene is polymerized to high molecular weight polyethylene.

39. A process according to claim 38, characterized in that propene is polymerized to vinyl terminated polypropylene.

40. A metallocene compound according to claim 2, wherein the transition metal of Group 4 or 5 of the Periodic Table is titanium, zirconium or hafnium.

41. A metallocene compound according to claim 3, wherein said one or two of $R_7$ to $R_9$ are a $C_5$–$C_{20}$ hydrocarbyl.

42. A metallocene compound according to claim 3, wherein said one or two of $R_7$ to $R_9$ are a phenyl.

43. A metallocene compound according to claim 4, wherein said hydroaromatic derivative ligand is 7,9-diphenylcyclopent[a]acenaphthadienyl ligand.

44. A metallocene compound acording to claim 6, wherein said $\eta^5$ ligand has two fused rings or three fused rings.

45. A metallocene compound according to claim 9, wherein said non-$\eta^5$ ligand is one of methyl and chlorine.

46. A metallocene compound according to claim 10, wherein the number of said non-$\eta^5$ ligands is 1 or 2.

47. A metallocene compound according to claim 14, wherein said alkylene bridge having from 1 to 10 carbons is an aromatically substituted alkylene bridge.

48. A metallocene compound according to claim 16, wherein said first bivalent group is bound to said transition metal.

49. A metallocene compound according to claim 17, wherein the number of said bridges is 0 to 1.

50. A metallocene compound according to claim 23, wherein at least one of $R_7$, $R_{7'}$, $R_9$ and $R_{9'}$ is a substituted or unsubstituted cyclic organic group having a substituted or unsubstituted aromatic group.

51. A metallocene compound according to claim 26, wherein said bridge Z is an alkylene bridge with a substituted or unsubstituted aromatic group.

52. An olefin polymerization catalyst composition according to claim 34, wherein said activator is an aluminoxane.

53. A process according to claim 37, wherein said at least one ethylenically unsaturated monomer is an olefin.

54. A process according to claim 38, wherein the ethene is polymerized to a polyethene having an average molecular weight of about 1,000,000 g/mol.

55. A process according to claim 39, wherein the propene is polymerized to branched polypropylene.

* * * * *